(12) United States Patent
Goeckner et al.

(10) Patent No.: US 11,510,660 B2
(45) Date of Patent: Nov. 29, 2022

(54) BIOPSY SAMPLE CONTAINER AND METHOD OF USE

(71) Applicant: Leica Biosystems Richmond, Inc., Richmond, IL (US)

(72) Inventors: Bruce A. Goeckner, Antioch, IL (US); Heather Renko-Breed, Rockton, IL (US); Randy Shanahan, Antioch, IL (US)

(73) Assignee: Leica Biosystems Richmond, Inc., Richmond, IL (US)

( * ) Notice: Subject to any disclaimer, the term of this patent is extended or adjusted under 35 U.S.C. 154(b) by 763 days.

(21) Appl. No.: 16/542,032

(22) Filed: Aug. 15, 2019

(65) Prior Publication Data

US 2020/0060661 A1 Feb. 27, 2020

Related U.S. Application Data

(60) Provisional application No. 62/723,359, filed on Aug. 27, 2018.

(51) Int. Cl.
   *G01N 1/00* (2006.01)
   *A61B 10/00* (2006.01)
   (Continued)

(52) U.S. Cl.
   CPC .......... *A61B 10/0096* (2013.01); *A61B 10/02* (2013.01); *B01L 3/508* (2013.01);
   (Continued)

(58) Field of Classification Search
   None
   See application file for complete search history.

(56) References Cited

U.S. PATENT DOCUMENTS

| 2014/0275999 A1 | 9/2014 | Speeg et al. |
| 2017/0137184 A1 | 5/2017 | Burek et al. |
| 2018/0000463 A1* | 1/2018 | Keller ................ A61B 10/0283 |

FOREIGN PATENT DOCUMENTS

| DE | 202018102561 U1 | 5/2018 |
| WO | 2017023666 A1 | 2/2017 |
| WO | 2018068210 A1 | 4/2018 |

OTHER PUBLICATIONS

"DuPont Engineering Polymers, General Design Principles—Module I", E.I. du Pont de Nemours and Company, p. 50, L-12565 03.02.

(Continued)

*Primary Examiner* — Jyoti Nagpaul
(74) *Attorney, Agent, or Firm* — Thompson Coburn LLP; William A. Holtz

(57) ABSTRACT

A sample container for use in imaging includes a bottom portion and a wall portion extending upwardly from the bottom portion. The lid overlies the cavity when in the closed position, and a plurality of latches are coupled to the lid and extend substantially orthogonally from the lid. A plurality of recesses are coupled to the wall portion, each recess of the plurality of recesses being adapted and configured to receive one of the plurality of latches. A first alignment structure is within the cavity and is adapted and configured to align a sample lengthwise and widthwise within the cavity such that the sample is aligned relative to an imaging system when the sample container is engaged with the imaging system. A second alignment structure is at least partially within the cavity, and is adapted and configured to align the sample height wise within the cavity.

20 Claims, 5 Drawing Sheets

(51) Int. Cl.
*A61B 10/02* (2006.01)
*B01L 3/00* (2006.01)
*G01N 1/28* (2006.01)
*A61B 17/00* (2006.01)

(52) U.S. Cl.
CPC ........ *G01N 1/28* (2013.01); *A61B 2010/0225* (2013.01); *A61B 2017/00477* (2013.01); *B01L 2200/025* (2013.01); *B01L 2300/043* (2013.01); *B01L 2300/046* (2013.01); *B01L 2300/0609* (2013.01)

(56) References Cited

OTHER PUBLICATIONS

"Snap-Fit Joints for Plastics, A Design Guide", Bayer MaterialScience LLC, pp. 8-17.
International Search Report and Written Opinion for PCT/US2019/046633 filed Nov. 21, 2019.

\* cited by examiner

BIOPSY SAMPLE CONTAINER AND METHOD OF USE

CROSS-REFERENCE TO RELATED APPLICATIONS

The present application claims the benefit of U.S. Provisional Patent Application Ser. No. 62/723,359, filed Aug. 27, 2018, which is incorporated herein by reference in its entirety.

BACKGROUND

This disclosure relates generally to a biopsy sample container, and more particularly, to a biopsy sample container for use with an X-Ray imaging device.

SUMMARY

In one aspect, a sample container for use in imaging includes a bottom portion and a wall portion extending upwardly from the bottom portion. The bottom portion and the wall portion define a cavity, and a lid is coupled to the wall portion and is positionable between a closed position and an open position. The lid is coupled to the wall portion by a hinge. The lid overlies the cavity when in the closed position, and a plurality of latches are coupled to the lid and extend substantially orthogonally from the lid. A plurality of recesses are coupled to the wall portion, each recess of the plurality of recesses being adapted and configured to receive one of the plurality of latches. Each latch of the plurality of latches is adapted and configured to engage with and disengage from a corresponding recess to releasably secure the lid in the closed position. A first alignment structure is within the cavity and is adapted and configured to align a sample lengthwise and widthwise within the cavity such that the sample is aligned relative to an imaging system when the sample container is engaged with the imaging system. A second alignment structure is at least partially within the cavity, and the second alignment structure is adapted and configured to align the sample height wise within the cavity such that the sample is aligned relative to the imaging system when the sample container is engaged with the imaging system.

In another aspect, a biopsy sample container for use with an X-Ray imaging device includes a bottom portion having a top side and a bottom side. The bottom side is opposite the top side. A wall portion extends upwardly from the top side of the bottom portion. The wall portion has an inner side and an outer side. The outer side is opposite the inner side. The top side of the bottom portion and the inner side of the wall portion at least partially define a cavity. A lid is coupled to the wall portion by at least one living hinge. The lid is positionable between a closed position and an open position. The lid overlies the cavity when in the closed position. At least one male snap fit latch portion is coupled to the lid and extends substantially orthogonally from the lid. At least one female snap fit latch portion is coupled to the inner side of the wall portion and corresponds to the at least one male snap fit latch portion. The female snap fit latch portion includes a catch, and the catch is positioned above a recess sized to accommodate at least a portion of the male snap fit latch portion. The male and female snap fit latch portions are adapted and configured to engage with and disengage from each other to releasably secure the lid in the closed position. A first alignment block is coupled to the top side of the bottom portion and extends upwardly into the cavity. A second alignment block is coupled to the top side of the bottom portion and extends upwardly into the cavity. The first and second alignment blocks are adapted and configured to align a tissue strip to a field of view of the X-Ray imaging device lengthwise and widthwise when the biopsy sample container is engaged with the X-Ray imaging device. A height location block is coupled to the top side of the bottom portion and extends upwardly into the cavity. A post is coupled to the lid and extends substantially orthogonally from the lid. The post is adapted and configured to bring a tissue strip lug into contact with the height location block when the lid is moved into the closed position such that the tissue strip is raised relative to the top side of the bottom portion into alignment height wise with a field of view of the X-Ray imaging device. The post is adapted and configured to secure the tissue strip between the post and the height location block when the lid is in the closed position.

In a further aspect, a method of using a biopsy sample container includes moving a lid of the biopsy sample container into an open position by disengaging at least one snap fit latch and rotating the lid relative to a bottom portion and wall portion of the biopsy sample container. The lid rotates about an axis defined by a living hinge coupling the lid to the wall portion. The method further includes placing a tissue sample within a cavity of the biopsy sample container. The cavity is defined by at least the bottom portion and wall portion of the biopsy sample container. The method still further includes aligning the tissue sample lengthwise and widthwise using at least one alignment block. The alignment block extends upwardly from the bottom portion of the biopsy sample container and into the cavity. The method still further includes arranging the tissue sample such that a tissue strip lug is positioned above a height location block. The height location block extends upwardly relative to the bottom portion of the biopsy sample container. The method also includes moving the lid from the open position toward the closed position such that a lid post contacts the tissue strip lug and lowers the tissue strip lug onto the height location block. The tissue strip is raised up relative to bottom portion of the biopsy sample container. The method further includes moving the lid portion into the closed position such that the at least one snap fit latch releasably secures the lid in the closed position. The at least one snap fit latch generates one or more of an audible indication and a tactile indication that the lid is in the closed position.

Further features and advantages of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the present disclosure and together with the description, serve to explain the principles of the disclosure. In the drawings.

DETAILED DESCRIPTION

Figure 1:
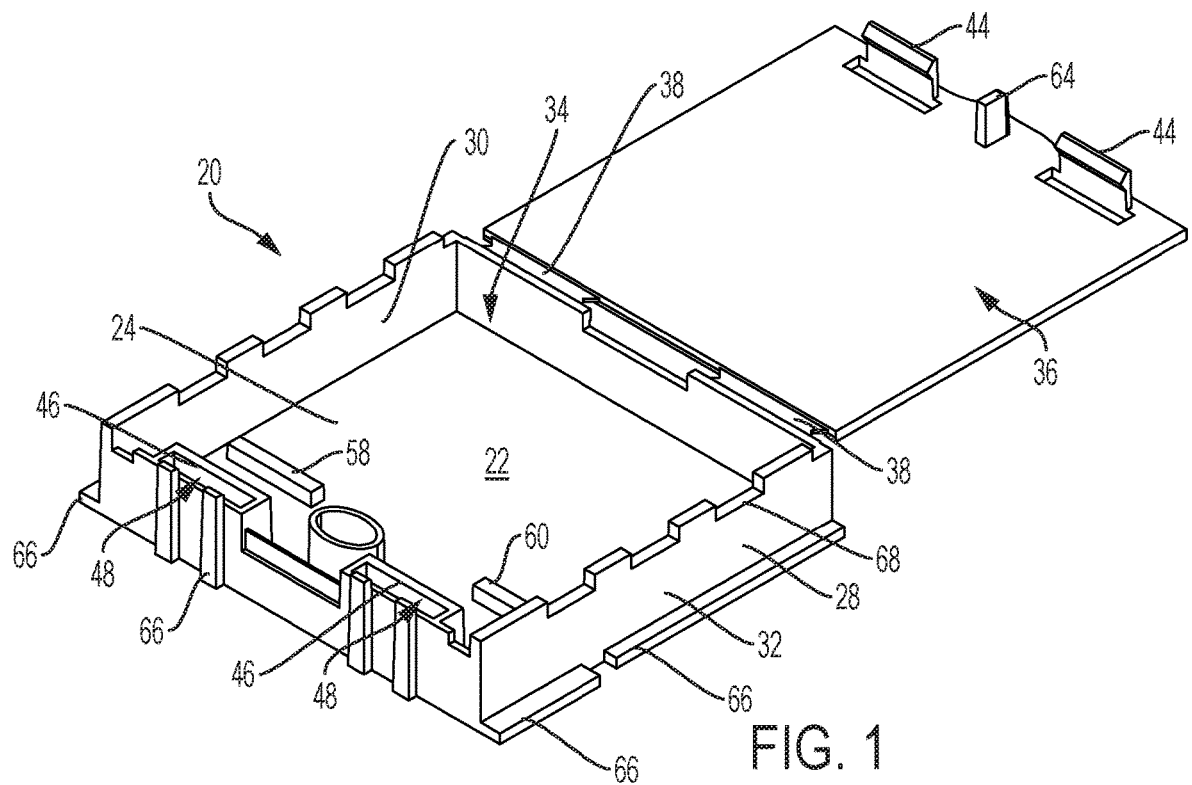
FIG. 1 is a perspective view showing one embodiment of a biopsy sample container in an open configuration.

Referring to the accompanying drawings in which like reference numbers indicate like elements, a biopsy sample container 20 for use with an X-Ray imaging device is depicted according to one embodiment. Generally, the container 20 allows for the storage and positioning of a sample, such as a tissue biopsy sample, such that the sample can be imaged by an imaging system (e.g., an X-Ray imaging system). It should be understood that the embodiment depicted and described is not limited to tissue samples and is not limited to use with X-Ray imaging systems. Any type of material (e.g., inorganic materials) may be used with the container 20 and the container 20 may be used with any type of imaging system (e.g., any microscopy system).

The container 20 includes a bottom portion 22 having a top side 24 and a bottom side 26. The bottom side 26 is opposite the top side 24. A wall portion 28 extends upwardly from the top side 24 of the bottom portion 22. The wall portion has an inner side 30 and an outer side 32. The outer side 32 is opposite the inner side 30. The top side 24 of the bottom portion 22 and the inner side 30 of the wall portion 28 at least partially defining a cavity 34. The cavity 34 is sized to accommodate a sample (not shown).

Figure 2:
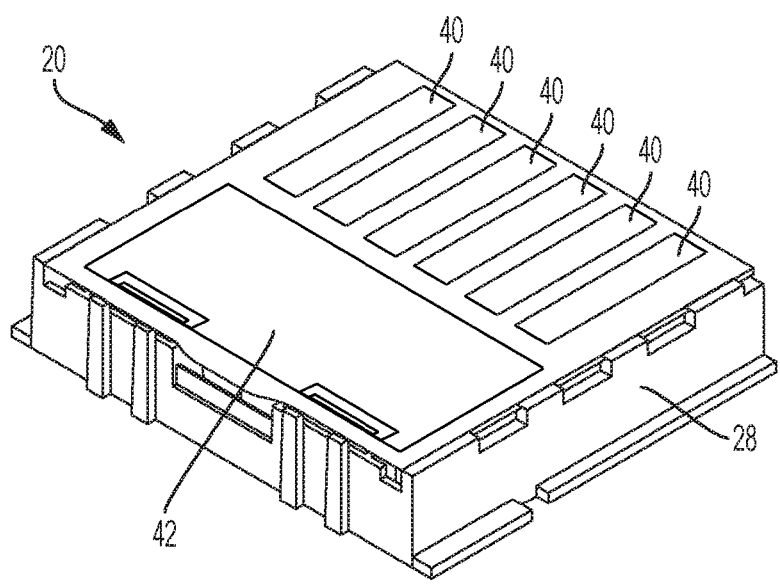
FIG. 2 is a perspective view of the biopsy sample container shown in FIG. 1, with the biopsy sample container in a closed configuration.
Figure 3:
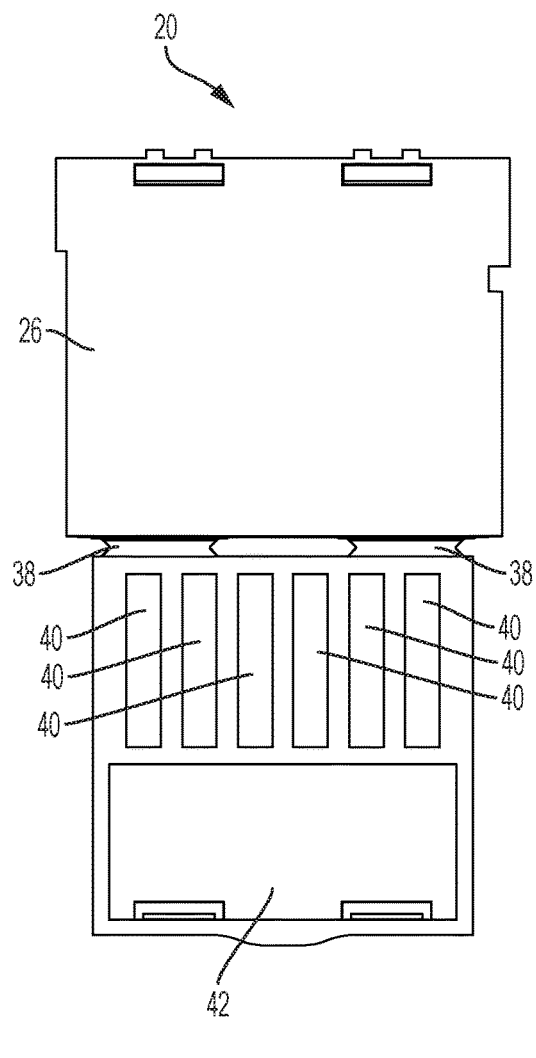
FIG. 3 is a top view of the biopsy sample container shown in FIG. 1.
Figure 4:
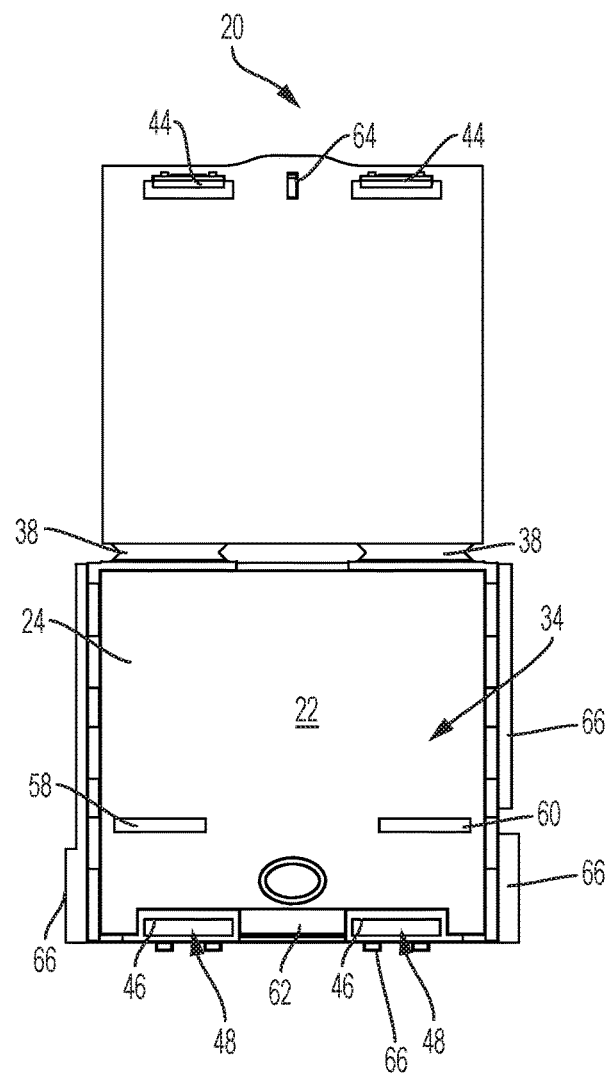
FIG. 4 is a bottom view of the biopsy sample container shown in FIG. 1.
Figure 5:
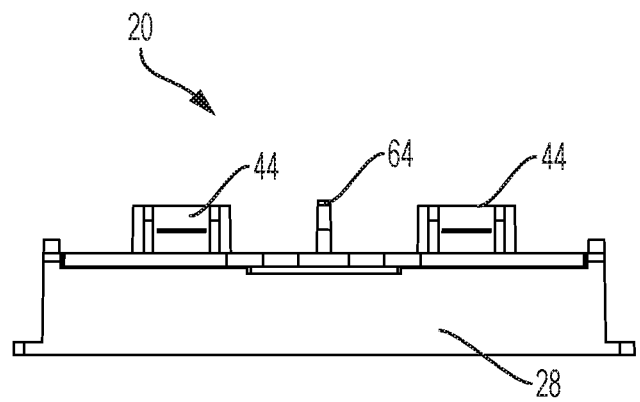
FIG. 5 is a rear view of the biopsy sample container shown in FIG. 1.
Figure 6:
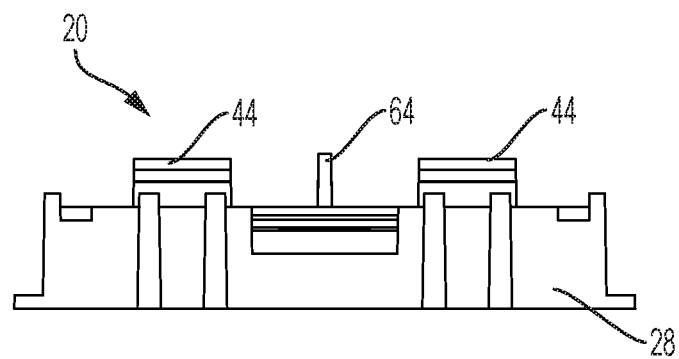
FIG. 6 is a front view of the biopsy sample container shown in FIG. 1.
Figure 7:
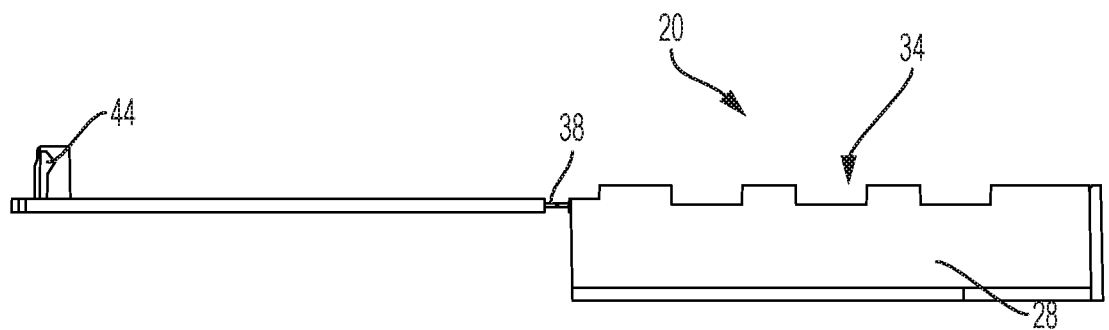
FIG. 7 is a left side view of the biopsy sample container shown in FIG. 1.
Figure 8:
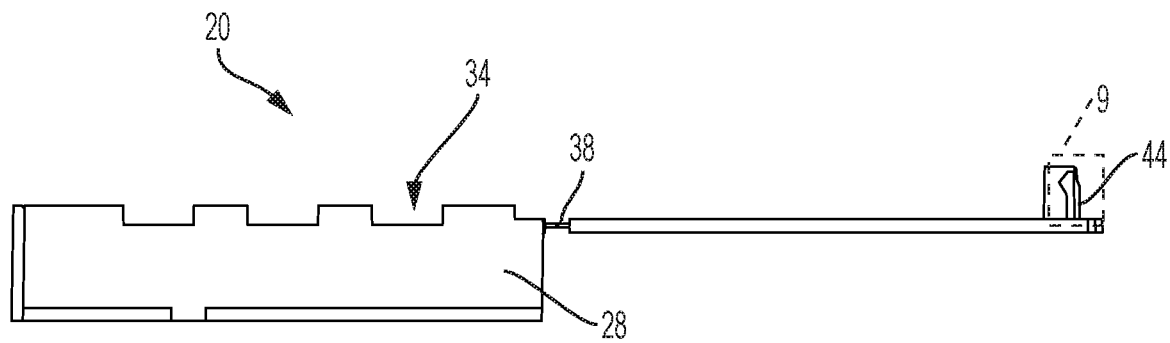
FIG. 8 is a right side view of the biopsy sample container shown in FIG. 1.
Figure 9:
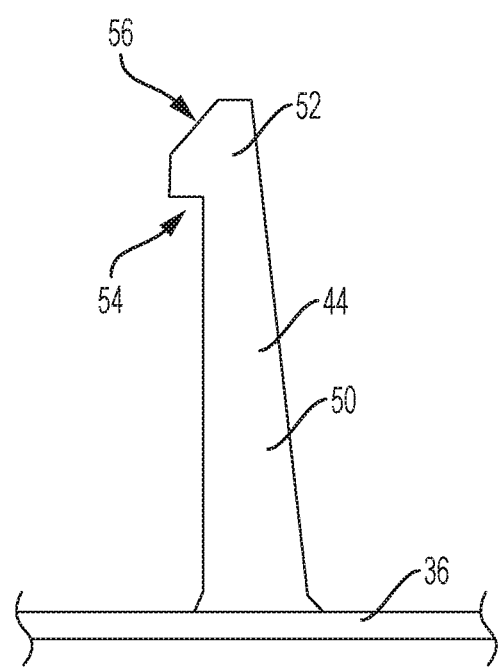
FIG. 9 is a detail view of a portion of a latch of the biopsy sample container shown in FIG. 1.

A lid 36 is coupled to the wall portion 28 by at least one living hinge 38. In the embodiment depicted, the lid 36 is coupled to the wall portion 28 by two living hinges 38. The lid 36 is positionable between a closed position (as shown in FIG. 2) and an open position (as shown in FIG. 1). The lid 36 overlies the cavity 34 when in the closed position. The lid 36 includes a plurality of embossed areas 40 arranged along a width of the lid 36 to enable labeling of areas of interest corresponding to a sample positioned within the cavity 34. The lid 36 further includes an additional embossed area 42 running along a portion of the width of the lid 36 to enable labeling of the sample container with identifying information. The plurality of embossed areas 40 are positioned closer to the hinge 38 lengthwise than the additional embossed area 42.

At least one male snap fit latch portion 44 is coupled to the lid 36 and extends substantially orthogonally from the lid 36. At least one female snap fit latch portion 46 is coupled to the inner side 30 of the wall portion 28 and corresponds to the at least one male snap fit latch portion 44. The female snap fit latch portion 46 includes a catch positioned above a recess 48 sized to accommodate at least a portion of the male snap fit latch portion 44. The male 44 and female 46 snap fit latch portions are adapted and configured to engage with and disengage from each other to releasably secure the lid 36 in the closed position.

In some embodiments, the snap fit latches are cantilever type laches. The male portions 44 include a cantilever beam portion 50 extending from the lid 36. The cantilever beam portion 50 may taper. The male portion 44 ends in a prong 52 having a cutout 54 and a chamfer 56. The chamfer 56 comes into contact with the catch of the female portion 46 of the latch as the lid 36 is closed. The chamfer 56 causes the cantilever beam portion 50 to deflect and allows the cutout 54 to pass the catch and engage with the catch to secure the lid 36. This configuration results in a force to engage the male snap fit latch portion 44 with the female snap fit latch portion 46 that is less than a second force to disengage the male snap fit latch portion 44 from the female snap fit latch portion 46. This configuration also results in a male snap fit latch portion 44 and a female snap fit latch portion 46 that are adapted and configured to provide audible and tactile feedback when engaging with one another to indicate that the lid 36 is in the closed position.

In some embodiments, such as the one depicted, the lid 36 includes two snap fit latches. It should be understood that fewer or more latches may be used in alternative embodiments. It should also be understood that other suitable latches may be used in alternative embodiments. For example, and without limitation, the latch(es) may be one or more of a press fit latch, cam lock, draw latch, spring latch, rotary latch, or other suitable latch.

The container 20 includes several alignment features for aligning a sample within the container 20 such that the sample is aligned with an imaging device field of view when the container 20 is engaged with the imaging device. A first alignment block 58 is coupled to the top side 24 of the bottom portion 22 and extends upwardly into the cavity 34. A second alignment block 60 is coupled to the top side 24 of the bottom portion 22 and extends upwardly into the cavity 34. The first 58 and second 60 alignment blocks are adapted and configured to align a tissue strip to a field of view of the X-Ray imaging device lengthwise and widthwise when the biopsy sample container 20 is engaged with the X-Ray imaging device. A height location block 62 is coupled to the top side 24 of the bottom portion 22 and extends upwardly into the cavity 34. A post 64 is coupled to the lid 36 and extends substantially orthogonally from the lid 36. the post 64 is adapted and configured to bring a tissue strip lug (not shown) into contact with the height location block 62 when the lid 36 is moved into the closed position such that the tissue strip is raised relative to the top side 24 of the bottom portion 22 into alignment height wise with a field of view of the X-Ray imaging device (or other device). The post 64 is also adapted and configured to secure the tissue strip between the post 64 and the height location block 62 when the lid is in the closed position. For example, and without limitation, the tissue sample lug is pinched between the height location block 62 and the post 64 when the lid 36 is in the closed position.

In some embodiments, the container 20 further includes one or more rails 66 for aligning the container 20 with the imaging device, storage rack, or the like. In some embodiments, the container 20 may include other features such as cutouts 68. Cutouts 68 are for fluid exchange after the X-ray imaging (or other device). This is after the container 20 is placed into a jar containing formalin for awaiting grossing of the tissue sample in a pathology laboratory. It should be understood that other optional features are contemplated and within the scope of the disclosure.

In operation, a method of using the container 20 includes moving the lid 36 of the biopsy sample container 20 into an open position by disengaging at least one snap fit latch and rotating the lid 36 relative to the bottom portion 22 and wall portion 28 of the biopsy sample container 20. The lid rotates about an axis defined by the living hinge 38 coupling the lid 36 to the wall portion 28. The method further includes placing a tissue sample within the cavity 34 of the biopsy sample container 20. The method still further includes aligning the tissue sample lengthwise and widthwise using at least one alignment block 58, 60. The method still further includes arranging the tissue sample such that a tissue strip lug is positioned above the height location block 62. The method also includes moving the lid 36 from the open position toward the closed position such that the lid post 64 contacts the tissue strip lug and lowers the tissue strip lug onto the height location block 62. The tissue strip is raised up relative to bottom portion 22 of the biopsy sample container 20. The method further includes moving the lid portion 36 into the closed position such that the at least one snap fit latch 44 releasably secures the lid 36 in the closed position. The at least one snap fit latch 44 generates one or more of an audible indication and a tactile indication that the lid is in the closed position. The container may then be placed in or otherwise engaged with an imaging device and the sample imaged. The container 20 may then be removed from the imaging device, the lid 36 opened, and the sample removed. The same container 20 may be used to image multiple different samples serially.

In view of the foregoing, it will be seen that the several advantages of the disclosure are achieved and attained.

The embodiments were chosen and described in order to best explain the principles of the disclosure and its practical application to thereby enable others skilled in the art to best utilize the disclosure in various embodiments and with various modifications as are suited to the particular use contemplated.

As various modifications could be made in the constructions and methods herein described and illustrated without departing from the scope of the disclosure, it is intended that all matter contained in the foregoing description or shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A sample container for use in imaging, the sample container comprising:
    a bottom portion, a wall portion extending upwardly from the bottom portion, the bottom portion and the wall portion defining a cavity, a lid coupled to the wall portion and positionable between a closed position and an open position, the lid coupled to the wall portion by a hinge, the lid overlying the cavity when in the closed position, a plurality of latches coupled to the lid and extending substantially orthogonally from the lid, a plurality of recesses coupled to the wall portion, each recess of the plurality of recesses adapted and configured to receive one of the plurality of latches, each latch of the plurality of latches adapted and configured to engage with and disengage from a corresponding recess to releasably secure the lid in the closed position, a first alignment structure being within the cavity, the first alignment structure adapted and configured to align a sample lengthwise and widthwise within the cavity such that the sample is aligned relative to an imaging system when the sample container is engaged with the imaging system, a second alignment structure being at least partially within the cavity, the second alignment structure adapted and configured to align the sample height wise within the cavity such that the sample is aligned relative to the imaging system when the sample container is engaged with the imaging system.

2. A sample container in accordance with claim 1, wherein the hinge is a living hinge.

3. A sample container in accordance with claim 1, wherein each latch of the plurality of latches is a snap fit latch, and wherein each recess of the plurality of recesses includes a catch corresponding to one of the snap fit latches.

4. A sample container in accordance with claim 1, wherein each latch of the plurality of latches is adapted and configured such that a force to engage with the corresponding recess to secure the lid in the closed position is less than a second force to disengage the latch from the recess.

5. A sample container in accordance with claim 1, wherein the second alignment feature aligns the sample height wise as the lid is moved into the closed position.

6. A sample container in accordance with claim 1, wherein each latch of the plurality of latches adapted and configured to provide audible and tactile feedback when engaging with the corresponding recess as the lid is moved to the closed position.

7. A sample container in accordance with claim 1, wherein the lid includes a plurality of embossed areas arranged along a width of the lid to enable labeling of areas of interest corresponding to a sample positioned within the cavity.

8. A sample container in accordance with claim 7, wherein the lid further includes an additional embossed area running along a portion of the width of the lid to enable labeling of the sample container with identifying information.

9. A sample container in accordance with claim 8, wherein the plurality of embossed areas are positioned closer to the hinge lengthwise than the additional embossed area.

10. A biopsy sample container for use with an X-Ray imaging device, the container comprising:
    a bottom portion having a top side and a bottom side, the bottom side opposite the top side, a wall portion extending upwardly from the top side of the bottom portion, the wall portion having an inner side and an outer side, the outer side opposite the inner side, the top side of the bottom portion and the inner side of the wall portion at least partially defining a cavity, a lid coupled to the wall portion by at least one living hinge, the lid positionable between a closed position and an open position, the lid overlying the cavity when in the closed position, at least one male snap fit latch portion coupled to the lid and extending substantially orthogonally from the lid, at least one female snap fit latch portion coupled to the inner side of the wall portion and corresponding to the at least one male snap fit latch portion, the female snap fit latch portion including a catch, the catch positioned above a recess sized to accommodate at least a portion of the male snap fit latch portion, the male and female snap fit latch portions adapted and configured to engage with and disengage from each other to releasably secure the lid in the closed position, a first alignment block coupled to the top side of the bottom portion and extending upwardly into the cavity, a second alignment block coupled to the top side of the bottom portion and extending upwardly into the cavity, the first and second alignment blocks being adapted and configured to align a tissue strip to a field of view of the X-Ray imaging device lengthwise and widthwise when the biopsy sample container is engaged with the X-Ray imaging device, a height location block coupled to the top side of the bottom portion and extending upwardly into the cavity, and a post coupled to the lid and extending substantially orthogonally from the lid, the post adapted and configured to bring a tissue strip lug into contact with the height location block when the lid is moved into the closed position such that the tissue strip is raised relative to the top side of the bottom portion into alignment height wise with a field of view of the X-Ray imaging device, the post adapted and configured to secure the tissue strip between the post and the height location block when the lid is in the closed position.

11. A biopsy sample container in accordance with claim 10, wherein the first and second alignment blocks are parallel with each other.

12. A biopsy sample container in accordance with claim 10, wherein the height location block is further coupled to the inner side of the wall portion.

13. A biopsy sample container in accordance with claim 10, further comprising a second living hinge coupling the lid to the wall portion.

14. A biopsy sample container in accordance with claim 10, comprising two male snap fit latch portions and two female snap fit latch portions.

15. A biopsy sample container in accordance with claim 10, wherein the male snap fit latch portion and the female snap fit latch portion are adapted and configured to provide audible and tactile feedback when engaging with one another to indicate that the lid is in the closed position.

16. A biopsy sample container in accordance with claim 10, wherein the lid includes a plurality of embossed areas arranged along a width of the lid to enable labeling of areas of interest corresponding to a sample positioned within the cavity.

17. A biopsy sample container in accordance with claim 16, wherein the lid further includes an additional embossed area running along a portion of the width of the lid to enable labeling of the sample container with identifying information.

18. A biopsy sample container in accordance with claim 17, wherein the plurality of embossed areas are positioned closer to the hinge lengthwise than the additional embossed area.

19. A biopsy sample container in accordance with claim 10, wherein the male and female snap fit latch portions are adapted and configured such that a force to engage the male snap fit latch portion with the female snap fit latch portion is less than a second force to disengage the male snap fit latch portion from the female snap fit latch portion.

20. A method of using a biopsy sample container, the method comprising:
- moving a lid of the biopsy sample container into an open position by disengaging at least one snap fit latch and rotating the lid relative to a bottom portion and wall portion of the biopsy sample container, the lid rotating about an axis defined by a living hinge coupling the lid to the wall portion;
- placing a tissue sample within a cavity of the biopsy sample container, the cavity defined by at least the bottom portion and wall portion of the biopsy sample container;
- aligning the tissue sample lengthwise and widthwise using at least one alignment block, the alignment extending upwardly from the bottom portion of the biopsy sample container and into the cavity;
- arranging the tissue sample such that a tissue strip lug is positioned above a height location block, the height location block extending upwardly relative to the bottom portion of the biopsy sample container;
- moving the lid from the open position toward the closed position such that a lid post contacts the tissue strip lug and lowers the tissue strip lug onto the height location block, the tissue strip being raised up relative to bottom portion of the biopsy sample container; and
- moving the lid portion into the closed position such that the at least one snap fit latch releasably secures the lid in the closed position, the at least one snap fit latch generating one or more of an audible indication and a tactile indication that the lid is in the closed position.

\* \* \* \* \*